(12) United States Patent
Massad

(10) Patent No.: US 6,186,788 B1
(45) Date of Patent: Feb. 13, 2001

(54) LINGUAL OCCLUSAL BUR

(75) Inventor: Joseph J. Massad, Tulsa, OK (US)

(73) Assignee: Massad Enterprises, Inc., Tulsa, OK (US)

( * ) Notice: Under 35 U.S.C. 154(b), the term of this patent shall be extended for 0 days.

(21) Appl. No.: 09/383,766

(22) Filed: Aug. 26, 1999

(51) Int. Cl.$^7$ ..................................................... A61C 3/02
(52) U.S. Cl. ............................................. 433/165; 433/166
(58) Field of Search ................................... 433/165, 166, 433/125

(56) References Cited

U.S. PATENT DOCUMENTS

| | | | | |
|---|---|---|---|---|
| 703,063 | * | 6/1902 | Hawkins | 433/165 |
| 3,461,563 | * | 8/1969 | Nelson | 433/165 |
| 4,830,615 | * | 5/1989 | Feinman et al. | 433/166 |
| 5,779,476 | * | 7/1998 | Roetzer et al. | 433/166 |

* cited by examiner

Primary Examiner—John J. Wilson
Assistant Examiner—Melba Bumgarner
(74) Attorney, Agent, or Firm—Molly D. McKay

(57) ABSTRACT

A pair of dental burs for shaping mandibular teeth into the proper sloped configuration for lingual occlusion or denture teeth. The first bur is provided with a non-cutting central portion that is flanked by two slightly angled cutting surfaces, and the second bur is provided with a cutting central portion that is flanked by two slightly angled non-cutting surfaces. The angulation of the two cutting surfaces on the first bur may or may not match each other on a given set of burs, and the angulation of the two non-cutting surfaces on the second bur may or may not match each other on a given set of burs, but the angles of the cutting surfaces on the first bur match the angles of the non-cutting surfaces on the second bur. The burs are used sequentially; i.e. the first bur is used first and the second bur is used second, to achieve the desired slope and center floss for the mandibular teeth without cutting too deeply.

5 Claims, 2 Drawing Sheets

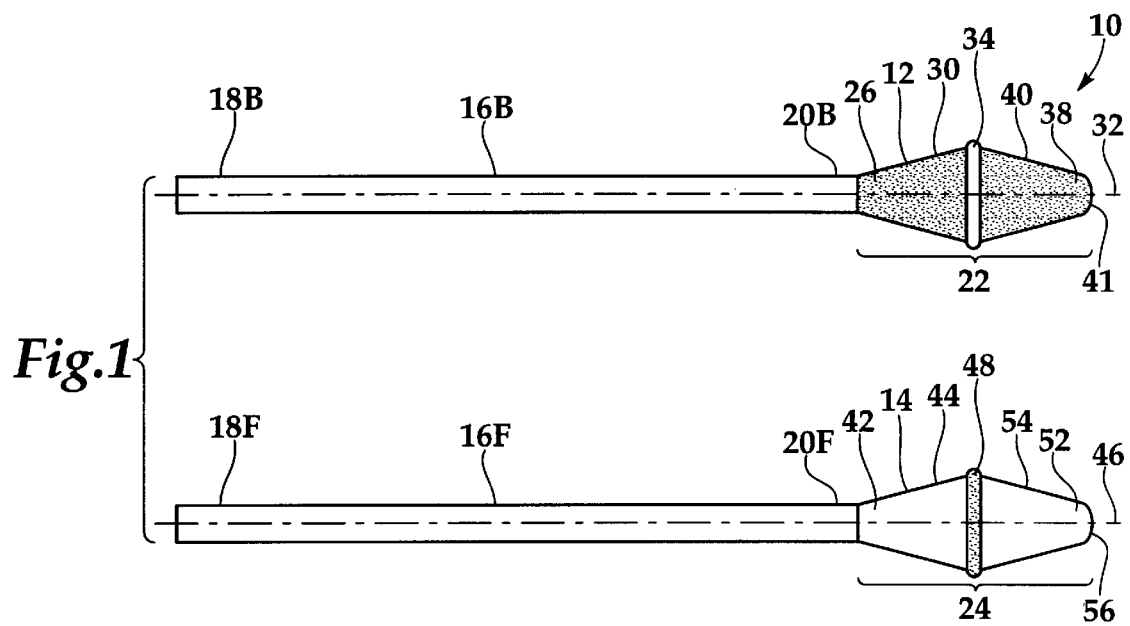
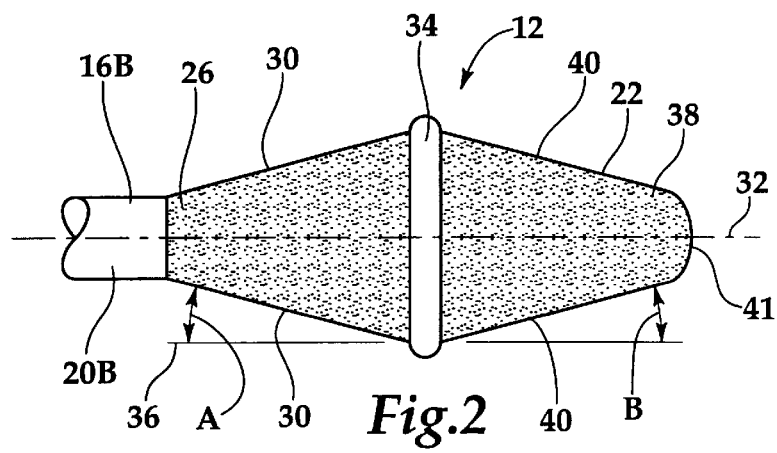
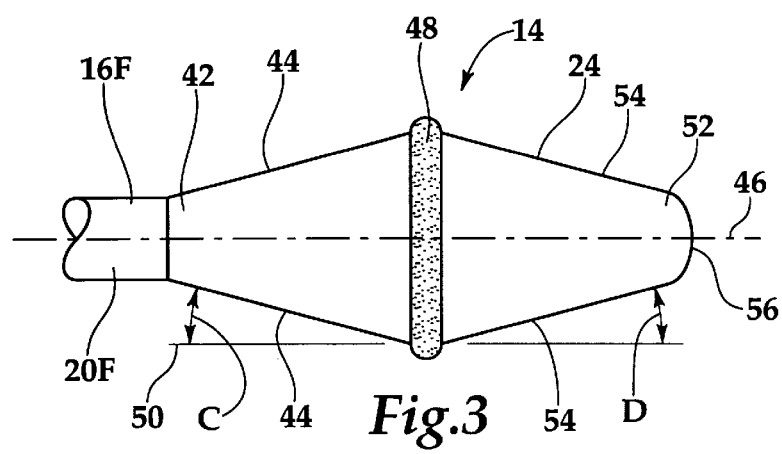

LINGUAL OCCLUSAL BUR

BACKGROUND OF THE INVENTION

1. Field of the Invention

The present invention relates to burs for grinding denture teeth. More specifically, the present invention relates to a pair of burs that can be used in conjunction to grind denture teeth so that the teeth have a lingual occlusion.

2. Description of the Related Art

For many years dental professionals have sought to produce dentures that would be esthetically pleasing, while still being comfortable and functional for the wearer. Many of the problems associated with dentures arise from the fact that the top denture plate is a unitary piece and the bottom denture plate is also a unitary piece and neither plate attaches securely in the wearer's mouth. Thus the top plate and the bottom plate each functions as a unitary tooth that can tip or rise up within the wearer's mouth.

For this reason, it is important that the teeth be positioned relative to each other to maximize chewing efficiency and to minimize tipping and raising up of the dentures. One of the more popular ways of making dentures is to make them with lingual occlusions. A lingual occlusion is where the maxillary lingual cusp is the dominant functional element, and occludes against the corresponding portion of the mandibular tooth. The mandibular teeth of a lingual occlusion are of two general types: they are either flat or they have a slight angulation. It is the latter group of dentures that the present invention is used to create, i.e. dentures with lingual occlusions that employ mandibular teeth with slight angulation and an area usually in the center of the lower tooth that will occlude with the upper tooth lingual cusp.

The angulation of the mandibular teeth in this type of lingual occlusion is slight so that the teeth can grind together to chew food without causing the plate to tip or be kicked up. The mandibular teeth must be shaped so that the fossae of the mandibular teeth are not too deep, the fossae properly receive the maxillary lingual cusps, and the angulation of the mandibular teeth is properly sloped. Currently, there are no burrs to allow a practitioner to quickly and accurately shape the mandibular teeth into the ideal sloped configuration.

The present invention addresses this problem by providing a pair of burs that can be used to shape the mandibular teeth into the proper sloped configuration required for lingual occlusion of the dentures. Specifically, the present invention is a pair of burs that include a first bur for cutting the cusps of the mandibular teeth while not cutting the fossa and a second bur for cutting the fossa of the mandibular teeth while not cutting the cusps. The first bur is provided with a non-cutting central port-on that is flanked by two slightly angled cutting surfaces, and the second bur is provided with a cutting central portion that is flanked by two slightly angled non-cutting surfaces. The burs are used sequentially; i.e. the first bur is used followed by use of the second bur, to achieve the desired slope and center fossa for the mandibular teeth for dentures.

The angulation of the two cutting surfaces on the first bur may or may not match each other on a given set of burs, and the angulation of the two non-cutting surfaces on the second bur may, or may not match each other on a given set of burs. However, the angulation of the slightly angled cutting surfaces provided on the first bur and the angulation of the slightly angled non-cutting surfaces provided on the second bur match each other for any given set of burs. It is important that the first and second burs in a set of burs match so that the non-cutting surfaces of the second bur will fit with the tooth after the tooth has been shaped with the cutting surfaces of the first bur and so that the non-cutting central portion of the first bur will fit with the tooth after the tooth has been shaped with the cutting central portion of the second bur, thus preventing the possibility of cutting away too much of the tooth.

SUMMARY OF THE INVENTION

The present invention is a new type of bur for shaping mandibular teeth in dentures into the proper sloped configuration required for a lingual occlusion. Specifically, the present invention is a matched pair of burs that include a first bur for cutting the cusps of the mandibular teeth while not cutting the fossa and a second bur for cutting the fossa of the mandibular teeth while not cutting the cusps. The first bur is provided with a non-cutting central portion that is flanked by two slightly angled cutting surfaces, and the second bur is provided with a cutting central portion that is flanked by two slightly angled non-cutting surfaces. The burs are used sequentially, i.e. the first bur is used and then the second bur is used, to achieve the desired slope and center fossa for the mandibular teeth for dentures.

The angulation of the two cutting surfaces on the first bur may or may not match each other on a given set of burs, and the angulation of the two non-cutting surfaces on the second bur may or may not match each other on a given set of burs. However, for any given set of burs, the angulation of the slightly angled cutting surface on the distal end of the first bur matches the angulation of the slightly angled non-cutting surface on the distal end of the second bur. Also, for any given set of burs, the angulation of the slightly angled cuffing surface on the proximal end of the first bur matches the angulation of the slightly angled non-cutting surface on the proximal end of the second bur. Further, the non-cutting central portion of the first burr matches the cutting central portion of the second bur for a given set of burs. To prevent the possibility of cutting away too much of the tooth with the burs, it is important that the first and second burs in a set of burs match in the angulation of their cutting and non-cutting surfaces so that the non-cutting surfaces of the second bur will fit against the tooth after the tooth has been shaped with the cutting surfaces of the first bur and so that the non-cutting central portion of the first bur will fit with the tooth after the tooth has been shaped with the cutting central portion of the second bur.

BRIEF DESCRIPTION OF THE DRAWINGS

FIG. 1 is a side view of a set of lingual occlusal burs constructed in accordance with a preferred embodiment of the present invention.

FIG. 2 is an enlarged view of the lingual occlusal incline bur shown at the top of FIG. 1.

FIG. 3 is an enlarged view of the lingual occlusal fossa bur shown at the bottom of FIG. 1.

DETAILED DESCRIPTION OF THE PREFERRED EMBODIMENT THE INVENTION

Figure 4:
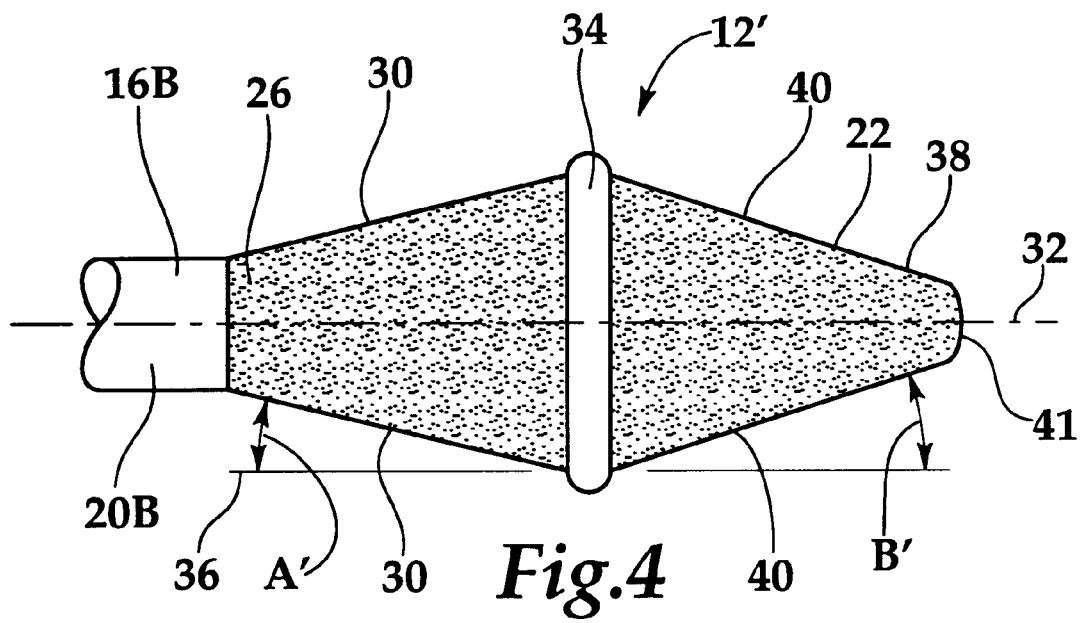
FIG. 4 is a side view of an alternate lingual occlusal incline bur from as second set of lingual occlusal burs.

Referring now to FIG. 1, there is illustrated a set of lingual occlusal burs 10 that are constructed in accordance with a preferred embodiment of the present invention. The set of lingual occlusal burs 10 consists of two burs: a first bur that is a lingual occlusal incline bur 12 and a second bur that is a lingual occlusal fossa bur 14.

The lingual occlusal incline bur 12 is provided with an incline shank 16B having a proximal end 18B for attachment to a drill (not illustrated) and an opposite distal end 20B. Likewise, the lingual occlusal fossa bur 14 is provided with a fossa shank 16F having a proximal end 18F for attachment to a drill (not illustrated) and an opposite distal end 20F. An incline bur head 22 is attached to the distal end of the fossa shank 16B, and a fossa bur head 24 is attached to the distal end of the shank 16F. The bur heads 22 and 24 may be constructed of any suitable material such as tungsten carbide or diamond, but diamond is the preferred material.

Referring now to FIG. 2, the construction of the incline bur head 22 of the lingual occlusal incline bur 12 is illustrated. A proximal end 26 of the incline bur head 22 attaches to the distal end 20B of its associated shank 16B. The proximal end 26 of the incline bur head 22 is provided with a first slightly angled cutting surface 30. The first slightly angled cutting surface 30 is provided symmetrically around a longitudinal axis 32 of the lingual occlusal incline bur 12 so that the first slightly angled cutting surface 30 extends between the distal end 20B of the shank 16B and a non-cutting central portion 34 provided centrally on the incline bur head 22. The non-cutting central portion 34 is also provided symmetrically around a longitudinal axis 32 of the lingual occlusal incline bur 12 and extends outward laterally beyond the rest of the incline bur head 22. The cutting surface 30 is at an angle A to a line 36, and line 36 is parallel to the longitudinal axis 32. Angle A may be any angle between approximately 1 and 30 degrees.

The opposite distal end 38 of the incline bur head 22 is provided with a second slightly angled cutting surface 40. The second slightly angled cutting surface 40 is provided symmetrically around the longitudinal axis 32 of the lingual occlusal incline bur 12 so that the second slightly angled cutting surface 30 extends distally from the non-cutting central portion 34, forming a tip 41 on the lingual occlusal incline bur 12. The cutting surface 40 is at an angle B to line 36. Angle B may be any angle between approximately 1 and 30 degrees. As illustrated in FIGS. 1–3, angles A and B may be the same angle for both of the cutting surfaces 30 and 40.

Referring now to FIG. 3, the construction of the fossa bur head 24 of the lingual occlusal incline bur 12 is illustrated. A proximal end 42 of the fossa bur head 24 attaches to the distal end 20F of its associated shank 16F. The proximal end 42 of the fossa bur head 24 is provided with a first slightly angled non-cutting surface 44. The first slightly angled non-cutting surface 44 is provided symmetrically around a longitudinal axis 46 of the lingual occlusal fossa bur 14 so that the first slightly angled non-cutting surface 44 extends between the distal end 20F of the shank 16F and a cutting central portion 48 provided centrally on the incline fossa head 24. The cutting central portion 48 is also provided symmetrically around the longitudinal axis 46 of the lingual occlusal fossa bur 14 and extends outward laterally beyond the rest of the fossa bur head 24. The first non-cutting surface 44 is at an angle C to a line 50, and line 50 is parallel to the longitudinal axis 46. Angle C may be any angle between approximately 1 and 30 degrees.

The opposite distal end 52 of the fossa bur head 24 is provided with a second slightly angled non-cutting surface 54. The second slightly angled cutting surface 54 is provided symmetrically around the longitudinal axis 46 of the lingual occlusal fossa bur 14 so that the second slightly angled non-cutting surface 54 extends distally from the cutting central portion 48, forming a tip 56 on the lingual occlusal fossa bur 14. The second non-cutting surface 54 is at an angle D to line 50. Angle D may be any angle between approximately 1 and 30 degrees. As illustrated in FIGS. 1–3, angles C and D may be the same angle for both of the non-cutting surfaces 44 and 54

Angle A is equal to angle C for a given set 10 of burs 12 and 14, and angle B is equal to angle D for a given set 10 of burs 12 and 14.

Figure 5:
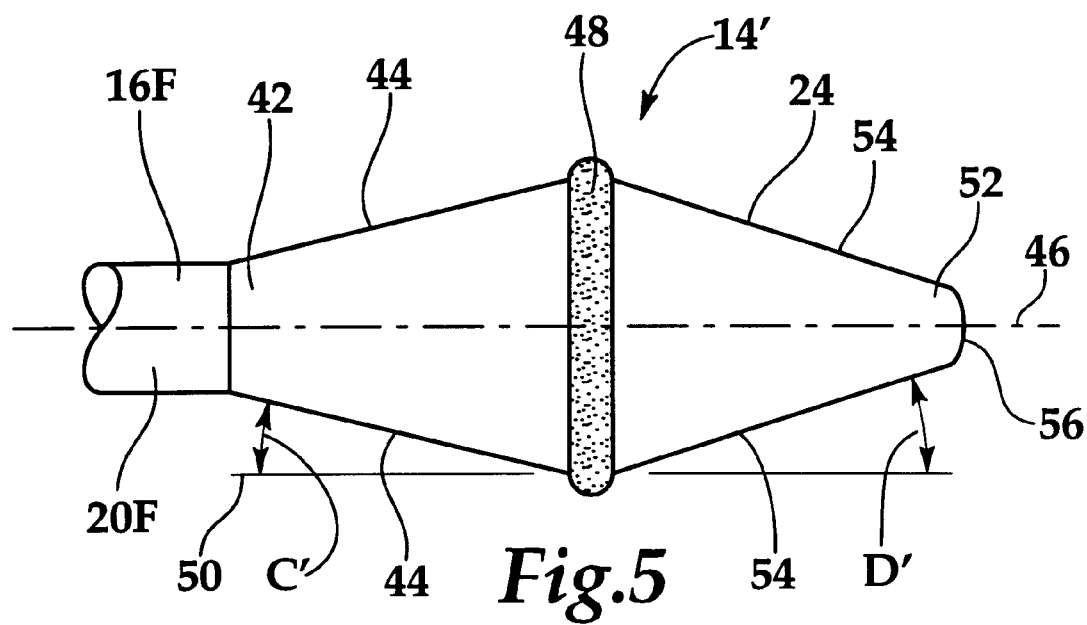
FIG. 5 is a side view of an alternate lingual occlusal fossa bur that is the mate to the alternate lingual occlusal incline bur of FIG. 4.

Referring now to FIGS. 4 and 5, there are illustrated, respectively, an alternate lingual occlusal incline bur 12' and an alternate lingual occlusal fossa bur 14'. The alternate burs 12' and 14' comprise an alternate set of lingual occlusal burs constructed in accordance with an alternate embodiment of the present invention. Alternate lingual occlusal incline bur 12' is identical to the lingual occlusal incline bur 12 previously described except for three features. First the alternate bur 12' is provided with an angle A' as the angle between the first slightly angled cutting surface 30 and the line 36 instead of angle A. Second, the alternate bur 12' provided with an angle B' as the angle between the second slightly angled cutting surface 40 and the line 50 instead of angle B. And third, angle A' is not equal to angle B'.

Alternate lingual occlusal fossa bur 14' is likewise identical to the lingual occlusal fossa bur 14 previously described except for substitution of angle C' for angle C' substitution of angle D' for angle D, and angle C' is not equal to angle D'. However, angle A' is still equal to angle C', and angle B' is still equal to angle D'. FIGS. 4 and 5 illustrate that angles A' and B' may be different from each other and that angles; C' and D' may be different from each other so long as angles A' and C' are equal to each other and so long as angles B' and D' are equal to each other.

A mating pair 10 of burs 12 and 14, or alternately 12' and 14', is employed to shape the mandibular teeth in dentures (not illustrated) into the proper sloped configuration required for lingual occluding of the denture teeth and for shaping a fossa therein. First, bur 12 or 12' is used. The non-cutting central portion 34 of the first mating lingual occlusal bur head, either 12 or 12' is guided along fossa in the posterior mandibular teeth in dentures (not illustrated) so that the cutting surfaces 30 and 40 simultaneously cut the buccal and lingual cusps of the posterior mandibular teeth into a v-shape. The slope of the v-shape that is formed is determined by angle A and angel B, or alternately by angle A' and B'.

Next, the bur 14 or 14' is used. The non-cutting surfaces 44 and 54 are guided along the previously shaped cusps of the posterior mandibular teeth so that the cutting central portion 48 cuts fossa in the posterior mandibular teeth. By sequentially using the burs 12 and 14, or alternately 12' and 14', the teeth are properly shaped but are not cut too deeply.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. Lingual occlusal burs for shaping denture teeth comprising:

a first bur provided with a first shank, a proximal end of said first shank for removable attachment to a drill and an opposite distal end of said first shank, a proximal end of a first bur head secured to said distal end of the first shank, a non-cutting central portion provided approximately midway between said proximal end of the first bur head and an opposite distal end of said first bur head, both said proximal end and said distal end of said first bur head provided with cutting surfaces, and each said cutting surface provided at an acute angle to a line parallel to a longitudinal axis of the first bur, and a second matching bur provided with a second shank, a proximal end of said second shank for removable attachment to a drill and an opposite distal end of said second shank, a proximal end of a second bur head secured to said distal end of the second shank, a cutting central portion provided approximately midway between said proximal end of the second bur head and an opposite distal end of said second bur head, both said proximal end and said distal end of said second bur head provided with non-cutting surfaces, and each said non-cutting surface provided at an acute angle to a line parallel to a longitudinal axis of the first bur.

2. Lingual occlusal burs for shaping denture teeth according to claim 1 further comprising:

said cutting surface on the proximal end of said first bur head forming a first angle with a line parallel to a longitudinal axis of the first bur, said cutting surface on the distal end of said first bur head forming a second angle with a line parallel to a longitudinal axis of the first bur, said non-cutting surface on the proximal end of said second bur head forming a third angle with a line parallel to a longitudinal axis of the second bur, said non-cutting surface on the distal end of said second bur head forming fourth angle with a line parallel to a longitudinal axis of the second bur, and said first angle being equal to said third angle and said second angle being equal to said fourth angle.

3. Lingual occlusal burs for shaping denture teeth according to claim 2 further comprising:

all said angles being between 1 and 30 degrees.

4. Lingual occlusal burs for shaping denture teeth according to claim 3 further comprising:

said non-cutting central portion and said cutting central portion being the same size, said non-cutting central portion extending outward laterally beyond the rest of the first bur head, and said cutting central portion extending outward laterally beyond the rest of the second bur head.

5. A method for shaping the mandibular teeth in dentures into the proper sloped configuration required for lingual occluding of the denture teeth and for shaping a fossa therein comprising the steps of:

a. guiding a non-cutting central portion of a first mating lingual occlusal bur head along fossa in the posterior mandibular teeth in dentures so that cutting surfaces provided on proximal and distal ends of the first mating lingual occlusal bur head cut cusps of the posterior mandibular teeth into a v-shape defined by a first angle formed between a line parallel to a longitudinal axis of the first bur head and the cutting surface on the proximal end of the first bur and by second angle formed between a line parallel to a longitudinal axis of the bur head and the cutting surface on the distal and of the first bur, and b. guiding non-cutting surfaces provided on proximal and distal ends of a second mating lingual occlusal bur head along previously shaped cusps of posterior mandibular teeth so that a cutting central portion provided on the second mating lingual occlusal bur head between the two non-cutting surfaces cuts fossa in the posterior mandibular teeth.

* * * * *